(12) United States Patent
Brumboiu et al.

(10) Patent No.: US 7,658,094 B2
(45) Date of Patent: Feb. 9, 2010

(54) SHEET-FORM MEMBRANE SAMPLE PROBE, METHOD AND APPARATUS FOR FLUID CONCENTRATION ANALYSIS

(75) Inventors: Aurel D. Brumboiu, Calgary (CA); Darrell A. Norquay, Calgary (CA); Bruce William, Calgary (CA)

(73) Assignee: DataLog Aquisition Corp.

( * ) Notice: Subject to any disclaimer, the term of this patent is extended or adjusted under 35 U.S.C. 154(b) by 577 days.

(21) Appl. No.: 11/423,217

(22) Filed: Jun. 9, 2006

(65) Prior Publication Data

US 2007/0000338 A1    Jan. 4, 2007

Related U.S. Application Data

(62) Division of application No. 10/707,902, filed on Jan. 22, 2004, now Pat. No. 7,111,503.

(51) Int. Cl.
*G01N 1/00* (2006.01)
(52) U.S. Cl. .................. 73/64.56; 73/53.01
(58) Field of Classification Search ............... 73/64.56, 73/63.1, 61.54, 863.23
See application file for complete search history.

(56) References Cited

U.S. PATENT DOCUMENTS 3,830,106 A * 8/1974 Gardiner et al. .......... 73/863.23
3,926,551 A * 12/1975 Lucero ..................... 436/178

(Continued)

FOREIGN PATENT DOCUMENTS

CA    2128329    9/1993

(Continued)

OTHER PUBLICATIONS

Supported Capillary Membrane Sampling Operation Manual, Global FIA, Inc., Jul. 12, 1999, pp. 1-14.

(Continued)

*Primary Examiner*—Hezron Williams
*Assistant Examiner*—Gunnar J Gissel
(74) *Attorney, Agent, or Firm*—Sean W Goodwin (57) ABSTRACT

A sheet form membrane probe, an apparatus and method, wherein the probe includes a probe body, a sheet-form membrane secured to the probe body and including an open surface exposed to the exterior of the probe; a channel formed between the probe body and the membrane through which a collector fluid can flow; an inlet port opening to the channel to conduct collector fluid to the channel; and an outlet port spaced from the inlet port such that the collector fluid passes through the channel from the inlet port to the outlet port in a flow direction substantially parallel to the membrane. The channel may be formed to provide broad surface contact of the collector fluid with the membrane. The membrane open surface may include an active area open to a sample fluid and open on an opposite side for contact with collector fluid flow in the channel. The active area may be large relative to the total membrane area to provide for an effective use of the expensive membrane material. Another probe includes a fitting end and a membrane stem and secures membranes to at least two sides of the membrane stem such that permeation can occur along a channel passing from the fitting end along the membrane stem and returning to the fitting end from the membrane stem.

21 Claims, 5 Drawing Sheets

U.S. PATENT DOCUMENTS

| | | |
|---|---|---|
| 5,000,051 A | 3/1991 | Bredemeier |
| 5,054,328 A * | 10/1991 | Long et al. ............... 73/864.81 |
| 5,317,932 A | 6/1994 | Westlake, III et al. |
| 5,442,968 A | 8/1995 | Westlake, III et al. |
| 5,448,062 A * | 9/1995 | Cooks et al. ................ 250/288 |
| 5,469,917 A | 11/1995 | Wolcott |
| 5,487,312 A * | 1/1996 | Kahl et al. ............... 73/863.01 |
| 5,553,484 A | 9/1996 | Bender et al. |
| 5,749,942 A | 5/1998 | Mattis et al. |
| 5,804,743 A * | 9/1998 | Vroblesky et al. ....... 73/863.23 |
| 5,876,604 A | 3/1999 | Nemser et al. |
| 5,902,747 A | 5/1999 | Nemser et al. |
| 5,914,154 A | 6/1999 | Nemser |
| 6,322,698 B1 | 11/2001 | Rios et al. |
| 6,397,689 B1 | 6/2002 | Moles |
| 6,439,027 B1 * | 8/2002 | Hiss, III .................... 73/28.01 |
| 6,562,211 B1 | 5/2003 | Kunnecke et al. |
| 2001/0008614 A1 | 7/2001 | Aronowitz |
| 2002/0056371 A1 | 5/2002 | Hayes |
| 2002/0184956 A1 * | 12/2002 | Taylor et al. ............. 73/863.03 |
| 2003/0033935 A1 | 2/2003 | Hu |
| 2004/0089079 A1 * | 5/2004 | Engebretson ............ 73/863.23 |

FOREIGN PATENT DOCUMENTS

| | | |
|---|---|---|
| WO | WO 96/07885 | 3/1996 |

OTHER PUBLICATIONS

FIA/SIA Tutorial Lesson 3, Membrane Sampling Devices, Global FIA, Inc., 2003, pp. 1-4.

* cited by examiner

SHEET-FORM MEMBRANE SAMPLE PROBE, METHOD AND APPARATUS FOR FLUID CONCENTRATION ANALYSIS

CROSS REFERENCE TO RELATED APPLICATIONS

This is a divisional application of U.S. application Ser. No. 10/707,902, filed Jan. 22, 2004 now U.S. Pat No. 7,111,503 and presently pending.

BACKGROUND OF INVENTION

The present invention refers to a probe for detecting or monitoring components of interest in a fluid or other material aggregation using membranes. More particularly, the invention relates to a sheet-type membrane probe.

Membrane-based sampling probes can permit analyte collection with good filtering of the base fluid itself or other interferents (i.e. solids) that may affect, damage or interfere with the analyzer or require some further filtering. Membranes used in these probes may be known as permeation or diffusion membranes and may be made from any permeable, semi-permeable or diffusion materials. Membrane-based monitoring processes can easily be made continuous and the probe and the afferent analytical system can be separated from each other. The sample collection can take place through a collector fluid (also called a carrier or collection fluid) flowing between the probe and the analyzer, which collects the analytes, also termed permeates, permeating the membrane at the probe and returns them to the analyzer for analysis.

The use of membrane probes for analytical purposes requires particular parameter adjustments, especially when the analytes are to be extracted from liquids or liquids streams. For example, permeation of the analyte is driven by its partial pressure differential across the membrane wall. In order to keep it at maximal values the inner side of the membrane is swept using a collector fluid, such as for example an inert gas. The collector fluid provides for transport of the collected analytes to the analyzer. Thus, the partial pressure of the analytes cannot be higher than their partial pressure in the sample fluid outside the membrane. In the case of sampling from a gas mixture, the requirement for a partial pressure drop across the membrane translates into lower concentrations of analyte collected than analyte concentration in the sample fluid. Moreover the higher the collector flow rate (in order to achieve a short response time to the analyzer), the lower the concentration collected. These effects result in a membrane attenuation factor due to the collector fluid flow.

In harsh industrial applications such as drilling fluid monitoring, the membrane may be required to withstand very adverse conditions like solid cuttings flowing together with the liquid mud, high pressures, intermittent pressure peaks, high liquid viscosity, etc.

In order for such a membrane-based sampling probe to achieve acceptable performance, it is desired to employ a membrane with a minimal thickness but capable of withstanding accidental mechanical hits and fluid abrasion. The membrane can include an active area in contact on one side with the sample fluid and on the other side with the collector fluid. Oftentimes it is necessary that the probe carrying the membrane be small enough for installation through the wall of a process vessel (pipe tank, reactor, etc). In view of the desirability of a probe having a maximal active area and small insert diameter, longitudinal shaped probes were developed where the diameter of the membrane supporting part is smaller than the diameter of the end fitting. This allowed probe replacement from the outside of the process vessel and facilitated sealing about the probe.

Some previous probes are described in U.S. Pat. Nos. 5,317,932 and 5,442,968 both of Westlake III, et al.; and U.S. Pat. No. 5,469,917 of Wolcott. These probes use capillary tubing shaped membranes laid on grooves in a membrane support body on the probe. The grooves provide a mechanical protection for the membrane tubing. However, the tubing-in-groove geometry forms hidden (dead flow) spaces between the tubing and the groove lateral walls and/or groove roots which spaces limit the active surface area of the membrane. In addition, the undulating surface can create a significant fluid boundary layer through which the analytes must pass in order to reach the membrane, especially, for example, where the sample fluid is a viscous liquid.

The function of tubing-based membrane probes can also be limited by high pressure applications, where the tubing collapses in certain pressures. Pressure collapse withstanding is generally a function of wall thickness, membrane type and tubing inner/outer diameter. However, membrane tubing having higher wall thickness often exhibit poorer permeation characteristics. It is possible to increase a tubing pressure performance by increasing the collector fluid pressure, possibly resulting in unfavorable analyte dilution effects Another challenge in using membrane probe devices for sampling relates to the transport time between the probe and the analyzer. This is especially relevant where the probe and analyzer are required to operate when spaced at more significant distances. In order to obtain a short transport (and implicitly response) time it is oftentimes necessary to increase the collector fluid flow rate. However, in this case an undesirably high head pressure may be required to pass the pneumatic resistance of the tubing or the tubing may tend to fail by blowing out.

The foregoing head pressure problems can be overcome to some degree by providing a plurality of membrane flow paths in parallel on the probe. Such a probe using capillary membranes is described in U.S. Pat. No. 5,553,484 of Bender et al., where multiple capillary tubings are mounted in a parallel flow configuration with each other. However, this probe, and its methods of manufacture and eventual tubing replacement procedures may be quite complex.

Some probes employ sheet-type membranes, rather than membranes of capillary tubing. The use of sheet-type membrane materials may improve the fluid flow characteristics over a probe's outer surface, when compared to capillary-based systems. In addition, there are generally more sheet-type membrane material options than for capillary membranes. Some probes using sheet-type membranes employ a disk shaped membrane geometry. One such embodiment is described in application WO96/07885 of Kristensen wherein the collector fluid flows through a narrow channel formed beneath the disk-shaped membrane. Other probes use a longitudinal membrane shape, termed herein ribbon-type. Such a probe is described in U.S. Pat. No. 6,562,211. While sheet-type membrane probes may address some of the liquid boundary layer problems of capillary type probes, the prior probes using sheet-type membranes continue to experience manufacture and low membrane active permeating surface area difficulties.

SUMMARY OF INVENTION

In the following, use of the terms "a" or "an" is intended to indicate one or more.

In one aspect of the present invention, there is provided a probe for analyzing fluid concentrations in a fluid to be analyzed, the probe including: a probe body; a sheet-form membrane secured to the probe body and including an open surface exposed to the exterior of the probe; a channel formed between the probe body and the membrane through which a collector fluid can flow; an inlet port opening to the channel to conduct collector fluid to the channel; and an outlet port spaced from the inlet port such that the collector fluid passes through the channel from the inlet port to the outlet port in a flow direction substantially parallel to the membrane; the channel being defined by a depth between the probe body and the membrane and a width extending substantially orthogonal to the flow direction between side limits of the channel and the width being at least 5 times greater than the depth; and the membrane open surface includes an active area open to the fluid to be analyzed and open on an opposite side for contact with collector fluid flow in the channel and the active area is at least 20% of the total membrane area.

In another aspect of the present invention, there is provided a probe for analyzing fluid concentrations in a fluid to be analyzed, the probe including: a probe body including a fitting end and a stem, the stem including an outboard end opposite the fitting end, a first side and a second side; a channel formed along the stem on its first side and second side, the channel extending along the first side from an inlet adjacent the fitting end toward the stem outboard end and passing to the second side to extend from the outboard end to an outlet adjacent the fitting end and the channel being formed on the stem surface at along a portion of its length; and a sheet-form membrane secured to the stem in a sealing configuration over the channel such that a collector fluid can pass through the channel from the inlet to the outlet, the membrane including an open surface exposed to the exterior of the probe and the collector fluid being in contact with the membrane inner surface when passing through the channel.

In another aspect of the present invention, there is provided a probe for analyzing fluid concentrations in a fluid to be analyzed, the probe including: a probe body including a fitting end and a membrane stem; a first membrane secured to the membrane stem of the probe body, the first membrane being a sheet-form semi permeable type membrane and including an open surface exposed to the exterior of the probe; a first channel formed between the probe body and the first membrane through which a collector fluid can flow; an first channel inlet port opening to the first channel to permit flow of collector fluid to the first channel; and a first channel outlet port spaced from the first channel inlet port such that the collector fluid passes through the first channel from the first channel inlet port to the first channel outlet port beneath the first membrane; a second membrane secured to the membrane stem of the probe body, the second membrane being a sheet-form semi permeable type membrane and including an open surface exposed to the exterior of the probe; a second channel formed between the probe body and the second membrane through which a collector fluid can flow; an second channel inlet port opening to the second channel to permit flow of collector fluid to the second channel; and a second channel outlet port spaced from the second channel inlet port such that the collector fluid passes through the second channel from the inlet port to the outlet port in a flow direction beneath the second membrane; a communication conduit providing fluid communication between the outlet port of the first channel and the inlet port of the second channel such that collector fluid from the first channel can flow through the hole to the second channel; an inlet conduit in communication with the first channel inlet port; and an outlet conduit in communication with the second channel outlet port; the inlet conduit and the outlet conduit each opening on the fitting end.

In accordance with another broad aspect of the present invention, there is provided a method of analyzing a fluid for the existence of a component of interest, the method including: using a sample probe having a sheet-form membrane mounted thereon; inserting the probe to the fluid so that at least the active area of the membrane is in contact with it; providing a collector fluid to the probe, the collector fluid passing through and exiting the probe; and, passing the exiting collector fluid on for analysis.

In accordance with another broad aspect of the present invention, there is provided an apparatus for analyzing a fluid for a component of interest, the apparatus comprising: a sample probe having a sheet-form membrane mounted thereon; a mounting configuration to install the probe in the process fluid to be analyzed; a main unit including any of an analyzer, a flow conditioning/measuring device for a collector fluid, and/or a power supply; and connections between the main unit and the probe including an incoming flow line from the main unit to the probe and an outcoming flow line from the probe to the main unit.

In accordance with another broad aspect of the present invention, there is provided a method of analyzing a fluid for the existence of a component of interest, the method including: providing a membrane probe including a membrane permeable to the component of interest; providing an analyzer, the analyzer being effective at a selected concentration range for the component of interest; inserting the probe to the sample fluid so that at least the active area of the membrane is in contact with the sample fluid; providing a collector fluid to the probe, the collector fluid passing through and exiting the probe; passing the exiting collector fluid to the analyzer for analysis for determination of the measured concentration of the component of interest; and adjusting the collector fluid flow rate to bring the measured concentration into the selected concentration range.

BRIEF DESCRIPTION OF DRAWINGS

Drawings are included showing various illustrative embodiments of the invention, as follows.

DETAILED DESCRIPTION

A probe according to one embodiment is shown in various configurations in FIGS. 1 to 8. While that one embodiment is shown and hereinafter described, it is to be understood that the probe can assume other shapes, orientations, configurations, with more or fewer parts and still remain within the invention, as claimed.

Referring to FIGS. 1 to 8, a membrane-based probe 1 is shown which is useful for fluid analysis. The fluid to be analyzed may contain one or more of a gas, a liquid or a solid in any form, including for example, pure form, mixtures, material aggregates, solutions, slurries, etc. The form of analysis may include, for example, detecting, measuring, sampling, filtering or determining the existence of one or more components (gas, vapor and/or liquid) of interest in the fluid. The fluid to be analyzed may be in various forms and conditions for example, it may be in a natural state, in an open or closed process, in a container such as a vessel, a pipe, a tank, etc. The analysis may be conducted on a continuous or intermittent, batch basis.

Probe 1 may include a probe body defining a membrane stem 2 and a fitting end 4. A membrane may be mounted on membrane stem 2 and, thus, at least a portion of stem 2 may be brought into contact with a fluid to be analyzed. While only one membrane need be used for fluid analysis with the probe, the illustrated embodiment includes a first membrane 9a and a second membrane 9b. The structures surrounding these membranes are substantially symmetrical and therefore, the description will proceed based on membrane 9a.

Between membrane 9a and the probe body is defined a collection channel 12a through which collection fluid can flow during fluid analysis. Channel 12a is an interstice defined between membrane 9a and channel surface 14 on membrane stem 2 and between side edges defined by a seal between the membrane and probe body. In this embodiment the seal can be an o-ring 16 mounted in a gland 18. A frame 20 may clamp over membrane 9a forcing o-ring 16 into sealing position between the probe body and the membrane.

For channel 12a, the collector flow input may be at one end and the output may be at the opposite end to create a collector flow substantially parallel to the membrane surface through the channel. Input flow enters channel 12a through an opening 22 from an inlet conduit 24 and output flow exits through one or more openings 26 at an end of the channel opposite from the position of opening 22. In the illustrated embodiment, wherein the probe is two-sided including the two membranes, openings 26 may at an end of one or more cross-over ports 28 passing to a channel 12b defined under membrane 9b. Channel 12b includes an opening 30 to a collector fluid outlet conduit 32. As such, collector fluid can flow in a circuit entering the probe through inlet conduit 24 and passing through channel 12a, cross-over ports 28 and channel 12b before exiting the probe through outlet conduit 32. In so doing, collector fluid sweeps past membranes 9a, 9b and collects permeate passing therethrough. The second membrane 9b and interstice channel 12b, being positioned on the return flow circuit avoids the need to form additional lengths of holes through or mount additional tubes along the probe body to return the collector fluid from the membrane stem and the second interstice channel can operate both for fluid transport and for permeation of components of interest. While a particular direction of flow has been described, it is to be understood that there may be no difference between inlet conduit 24 and outlet conduit 32 such that the fluid can circuit in a reverse direction, than that just described, through the probe if desired. It is also to be noted that although various numbers, positions and shapes of openings, ports and conduits have been shown, many other such numbers, positions and shapes are possible.

Membranes 9a, 9b are sheet-type, may be known as permeation or diffusion membranes and may be made from any permeable, semi-permeable or diffusion materials. The membranes can be selected depending, for example, on the parameters of the fluid and component to be analyzed, the form of analysis and the process conditions. In some embodiments, membranes 9a, 9b may be formed of ceramic, metals, polymers, etc. and may include one part sheets, laminates, composites (i.e. semi permeable material applied to or imbedded in a support, for example, mesh or porous substrate), or sandwich arrangements (i.e. one or more membrane sheets sandwiched with one or more supports or other sheet membranes. Sheet-form membranes may be reinforced by forming as laminates or composites. In one embodiment, a sheet-form membrane includes membrane material coating or infiltrating a stainless steel mesh. Such a membrane may exhibit enhanced strength, resistance to wear and durability over a non-reinforced membrane formed of a similar membrane material of a similar thickness.

The probe membranes permit permeation of components of interest from their outer-facing surface to their inner-facing surface where the components of interest are picked up by the collection fluid. Permeation may be proportional with the membrane active area and may diminish with increased membrane thickness. A membrane's active area, therefore, may be defined as that area open to the channel on its inner facing surface (one dimension of which is illustrated as 59i in FIG. 9) and open on the external surface of the probe on its outer facing side (one dimension of which is illustrated as 59o in FIG. 9). For effective use of the oftentimes expensive membrane material it is useful to maximize the membranes active surface area when compared to the overall surface area of the membrane. In one embodiment, it may be desirable that the active area be at least about 20% of the total membrane area. For example, in the illustrated embodiment the membrane's active surface area may be at least about 30% and in one embodiment may be at least about 40% to 50% of the total membrane surface area. Of course the active area relative to the overall membrane area in the illustrated embodiment could be further increased by reducing that portion of the membrane extending out beyond the seals, defined by O-rings 16. However, the extra edge portions of the membrane were selected to facilitate assembly.

Fitting end 4 offers a body portion for at least grasping and possibly mounting the probe for uses The fitting end can take many forms, depending on its intended function. For example, the probe may be used in a process wherein it is mounted in a vessel, for example, with fitting end 4 mounted in the wall and membrane stem 2 extending into the vessel inner volume, in which fluid to be analyzed is contained or flows. In such an embodiment, it is desirable that the maximum dimension, for example the diagonal distance $D_{mb}$ of the assembled probe at its membrane stem be less than the fitting end effective diameter $D_{fe}$, so that the stem can be inserted into the vessel through an opening sized to accept and fit about fitting end 4. The membrane stem longitudinal geometry, as shown, permits such an installation and geometry without jeopardizing active surface area. In addition, forming the membrane long and thin permits the membrane active area to be increased in size to get higher permeation by simply increasing the length, without a need for modification of the stem width.

Fitting end 4 accommodates inlet conduit 24, which opens at orifice 36 and outlet conduit 32, which opens at orifice 38.

Since both orifices 36, 38 of the probe open at one end, again installation of the probe in a process vessel is facilitated. The collector fluid flowing through the inlet conduit moves in a direction substantially opposite to the direction of fluid flow through the outlet hole. In the illustrated embodiment, the outlet conduit extends substantially parallel to the inlet hole. Fittings for tubing, etc. can be mounted at orifices 36, 38 to permit connection of the probe into a fluid analysis apparatus, as disclosed hereinbelow.

While a probe including two membranes has been illustrated, it is to be understood that the probe can take other configurations. For example, as previously mentioned, the probe can support a single membrane and associated collector fluid channel. To permit a flow circuit in such an embodiment, conduits 24 or 32 can be extended through body or other conduits can be connected to complete a fluid flow circuit through the probe. Alternately, more than two membranes could be mounted on the probe. In yet another alternative embodiment than that shown, two or more membranes and channels can be mounted on the probe and various fluid circuit holes can be formed through the probe body or through the use of additional conduits. For example, a probe may be provided including at least two different membranes with different permeation characteristics and an arrangement of circuit holes or conduits to transmitting two different collector flows separately or to be combined for various analytical purposes, for example, an enlarged permeate spectrum (i.e. more than one component of interest), differential or comparative analysis, etc.

It is desirable to form the probe body in one piece to avoid the need for seals at interfacing parts. Therefore, minimizing, when possible, the lengths of fluid circuit holes that must be drilled through the probe body, may facilitate manufacture.

In the illustrated embodiment as mentioned hereinabove, membranes 9a, 9b are secured onto membrane stem 2 by frames 20. The frames may be U-shaped, as shown, with a clamping part 42 and returns 44. Clamping part 42 at least in part overlies the edges of membrane, while returns 44 extend down over the sides of membrane stem 2. Although, the frames need not be U-shaped, the inclusion of a return 44 may assist with assembly and enhance the rigidity and, therefore, the operation of clamping part 42 to urge the membranes down against the probe body. Fasteners such as screws 46 engaged into threaded holes 48 from each side may secure frames 20. The fasteners can be positioned about each frame along the long sides and ends to securely compress O-rings 16 to form a continuous seal. Membrane placement can be facilitated by forming the membrane to extend out to the width between returns 44 so that it can be held in position within the frame during installation on the stem. Of course, it is to be understood that many other mounting arrangements can be used, as desired. For example, longer pass through bolts including nuts could be used that would act against both frames at the same time. Alternately, frames could be removed altogether and other methods (i.e. fusing, adhesives, etc. or components (straps, rivets, etc.) could be used. Also the membrane can be shaped with less consideration to the frame shape or other means can be used to assist with membrane placement.

The probe may be formed or positioned with consideration as to fluid flow there over to address or reduce boundary layer issues. For example, since the sheet-type membrane includes a generally planar surface with only a small perimeter frame, if any, extending about it, fluid flow can tend to pass smoothly thereover, especially, for example, when the flow passes along the length of the membrane. It may be useful, in the illustrated embodiment, to arrange the membranes to extend in substantially parallel planes to reduce the thickness of the probe and such that the probe can be more easily positioned in a process to select membrane orientation relative to the impingement and flow past of the fluid to be analyzed.

In the illustrated embodiment, channels 12a, 12b are sealed by o-ring type gaskets 16 in glands 18 and compressed by frames 20. Of course, other seal mechanisms may be used such as, for example, flat or liquid applied gaskets in a groove or on a flat probe body surface. Alternately, the edges of the membranes 9a, 9b may be sealed, as by adhesive or fusion, etc., directly to the probe body or to a gasket sealed, as by fusing or adhesives, to probe body.

The membrane sheet may be mounted on the probe body so that the interstice channel permits a substantially unobstructed collector fluid flow with a low pressure head. To achieve this, it is desirable that the channel be formed with a shallow depth, but a considerable width to permit the collector fluid to sweep over the membrane inner surface to effectively collect permeates. In one embodiment, the channel may be defined by (i) a depth D between the probe body and the membrane (best illustrated in FIG. 9) and (ii) a width W extending substantially orthogonal to the flow direction between side limits of the channel and the width may be at least 5 and possibly at least 10 times greater than the depth. Such an arrangement also may provide that the membrane is spaced to provide a channel for fluid flow and can flex to some degree, if pressure is applied thereto, but it may be supported against the probe body after slight planar deflection. This may support the membrane against damage in the case of accidental or intermittent mechanical impacts or outside pressure shocks thereagainst. Also, such an arrangement may provide for greater membrane contact per channel cross sectional flow area than that through a channel having a width that is more similar or less than that channel's depth. In the illustrated embodiment, o-rings 16 may space the membrane 0.1 to 0.2 mm above channel surface 14 and the channel has a width of 8 to 12 mm between the channel side limits, as defined by o-rings 16, such that the channel has a depth to width ratio of between about 1:40 to 1:120.

The probe configuration has been shown to permit collector fluid flow rate changes substantially without affecting the head pressure in the system. In addition, the permeating area, which is the membrane active area, of the probe can be increased again substantially without a significant increase in the head pressure for the collector.

Figure 1:
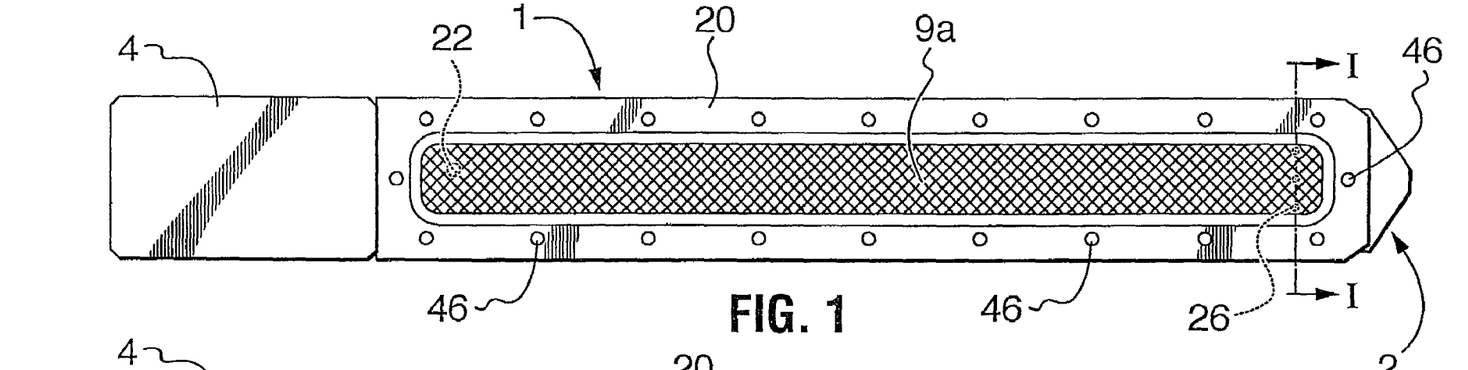
FIG. 1 is a top plan view of one embodiment of a probe according to the present invention.
Figure 2:
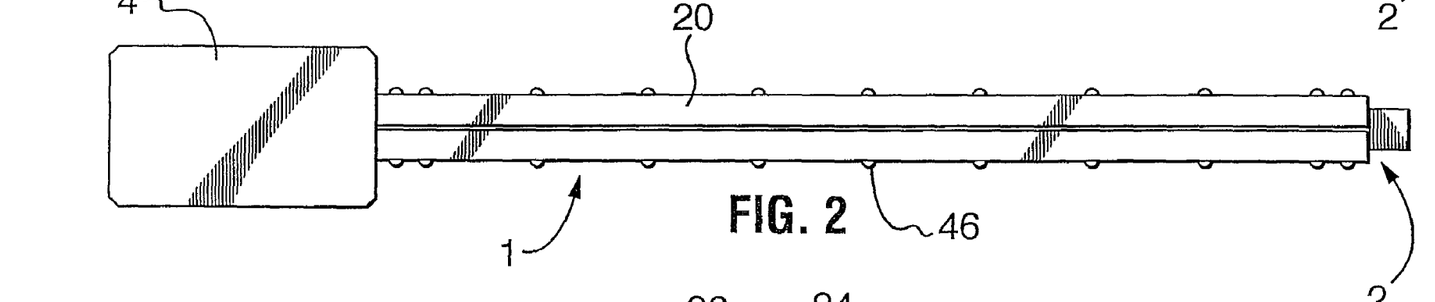
FIG. 2 is a side elevation of the probe of FIG. 1.
Figure 3:
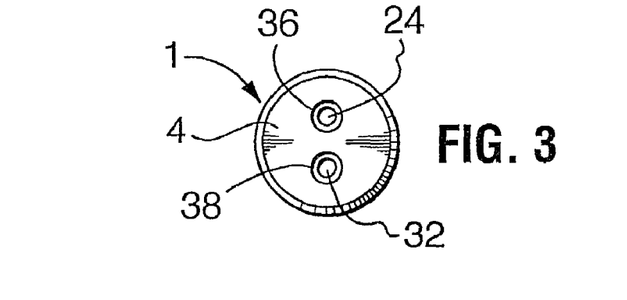
FIG. 3 is an end elevation of the probe of FIG. 1.
Figure 4:
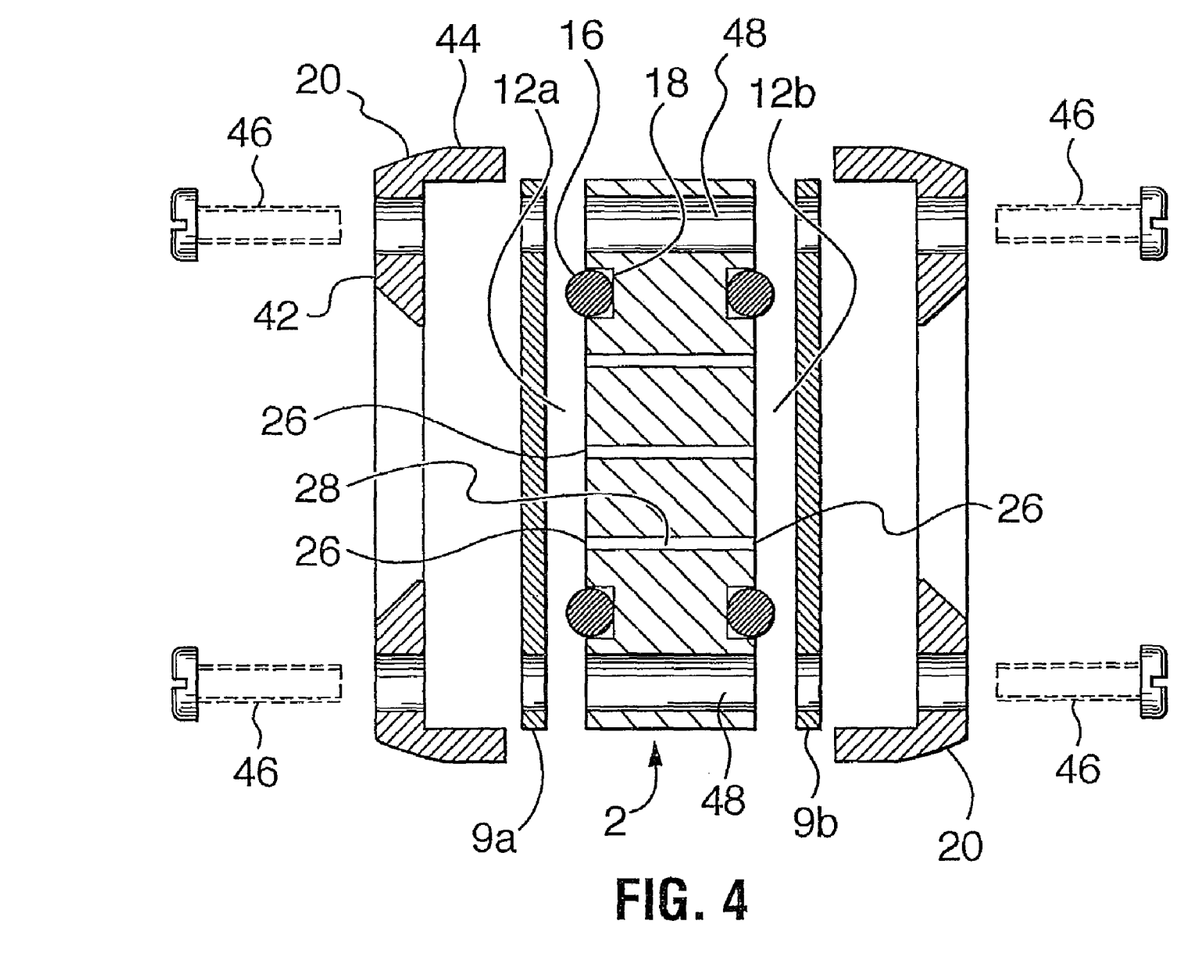
FIG. 4 is a section along line I-I of FIG. 1, with the probe components in exploded configuration, but aligned for assembly thereof.
Figures 5, 6, 7, 8:
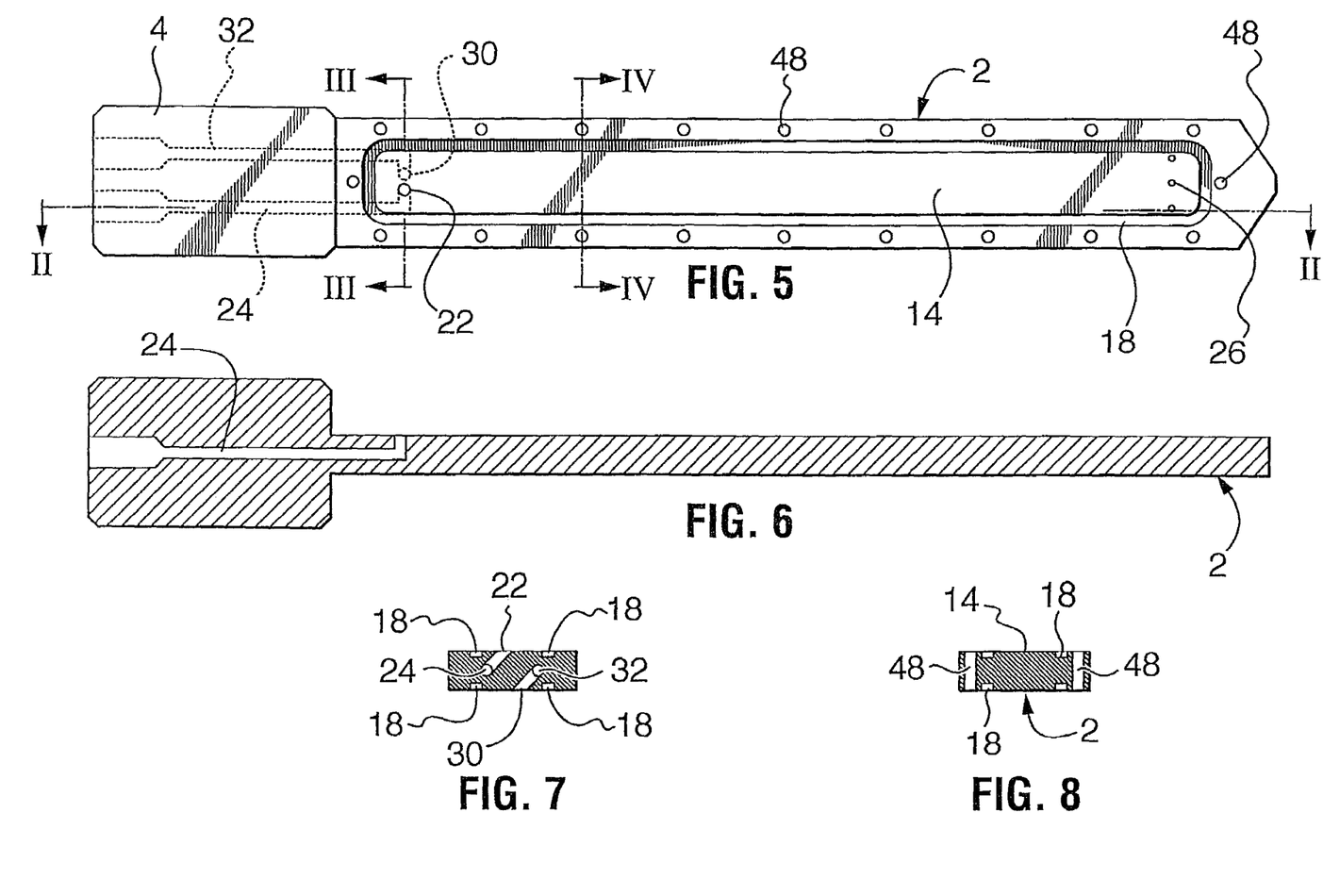
FIG. 5 is a top plan view of a probe body useful in a probe of FIG. 1.
FIG. 6 is a section along line II-II of FIG. 5.
FIG. 7 is a section along line III-III of FIG. 5.
FIG. 8 is a section along line IV-IV of FIG. 5.
Figure 9:
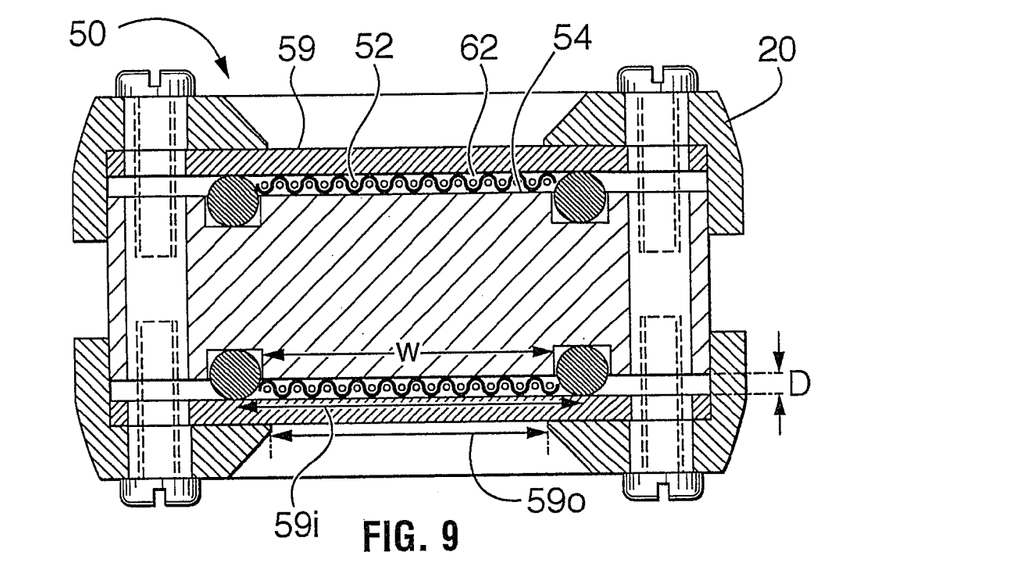
FIG. 9 is a section similar to FIG. 4 through another probe, but in assembled configuration.

In another embodiment, shown in FIG. 9, the membrane of a probe 50 may supported away from the probe body between its side limits to mitigate the adverse effects, including for example membrane damage or channel obstruction, due to an application of high external pressure against the membrane. In particular, in FIG. 9, a support screen 52 may been placed between channel surface 54 and membrane 59. The screen may be selected to support the membrane, beneath its active surface area, away from contact with the channel surface, but without blocking flow through channel 62. The screen may or may not extend the full depth between the membrane and the channel surface but may maintain the membrane spaced from channel surface 54 if mechanical or fluid pressure against membrane 59 causes it to flex inwardly.

Other membrane supports may include, for example, another mesh-like or porous material inserted between the membrane and the probe body. Alternately or in addition, a mesh-like or porous material can be partially embedded in the membrane such that protrusions of the material extend from the membrane to support the membrane away from the probe body. Such an approach may also serve to enhance the durability of the membrane, since the embedded material may increase the membrane strength against bending and/or breaking. This approach may be useful for membrane materials that can be, for example, coated, cured, polymerized, pressed or melt pressed onto the support material. Another membrane support may include protrusions formed to extend up on or form the channel surface between the channel side walls. Protrusions may be formed, for example, by building up, milling, etching, pitting, coarse sanding or knurling the probe surface.

All the above-mentioned supports can maintain an open flowing interstice and in the mean time to mechanically support the membrane from the inside. This offers the possibility of using thin membranes laid on long continuous channels to provide long exposed active membrane surfaces, but that can withstand high external pressures applied continuously or intermittently. In addition, supported membranes may provide higher breaking resistance over unsupported ones and may act against the partial or total channel obstruction by the membrane being forced to deflect inwardly. This keeps the interstice open for passage of the collector fluid. The support volume may be reduced in order to achieve a desired head pressure for collector fluid flow. Also it has been found that the support may cause turbulence in the collector fluid flow, enhancing permeate evacuation by better sweeping of the membrane inner surface over a laminar flow condition.

Based on such sampling probes, analytical methods and apparatus can be developed with wherein the probe and the analytical measuring equipment may be separated by a significant distance. Such methods and apparatus may, for example, be desirable when the sampling point is situated in a classified zone and it is desirable to have the analytical measuring system located out of that classified zone so that for example simpler equipment can be used, personnel safety or comfort is a consideration, etc.

Figure 10:
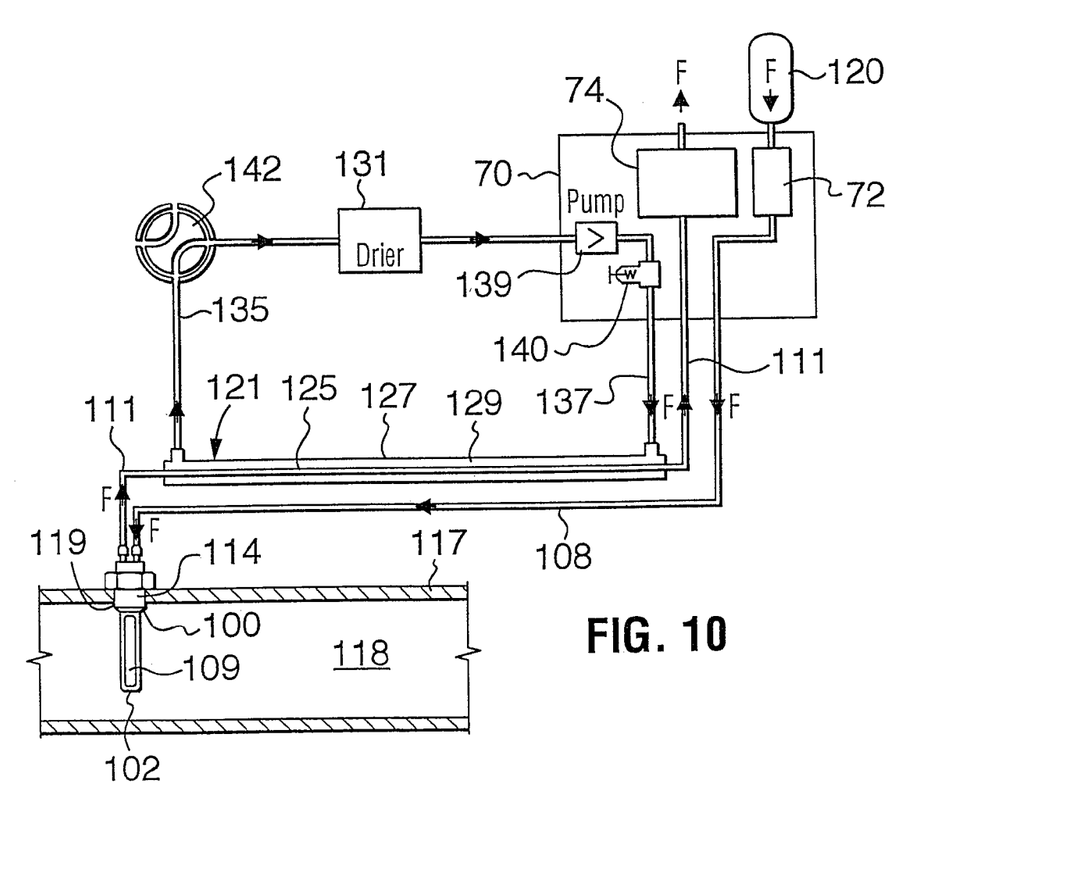
FIG. 10 is a schematic illustration of one embodiment of an apparatus according to the present invention employing a probe.

Referring to FIG. 10, an apparatus for fluid analysis may include a main unit 70 including one or more of collector flow conditioning means 72 (i.e. pumps, pressure regulators, mass flow controllers, pneumatic restrictions, valves, solenoid valves, etc.), input and/or output collector flow measuring means, concentration analyzers/detection means 74, power supplies, microprocessors and/or computer processing units and, in general, all the necessary electrical parts and connections. The apparatus further includes a membrane-based probe 100, that may, for example, be similar to one described in FIG. 1 or 9 with or without any of the various described or other options, at least one collector flow input line 108 from the main unit to the sampling probe and at least one output line 111, sometimes referred to as a return line, from the probe to the main unit. The lines can be selected to effectively transport the collector fluid and may be, for example, pneumatic.

Probe 100 may be used in any process fluid. For example, probe 100 may be used in a container such as a vessel, a pipe, a tank, etc. Probe 100 can be installed with its fitting end 114 mounted in a vessel wall 117 and with the active surface area of its membrane 109 in contact with a fluid 118 to be analyzed. End 102 of the probe on which membrane 109 is mounted has a maximum dimension less than that of the probe's fitting end 114, so that the probe can be installed through and mounted in an opening 119 sized to secure fitting end 114. Fitting end 114 can be formed in a number of ways to permit mounting. For example, fitting end and opening can include corresponding parts of a compression ferrule fitting, threads, flange mount connected by fasteners, keys or couplings, etc. Generally it is desirable that the fitting end mounting configuration include a sealing component to prevent escape of process fluids through the opening. Lines 108 and 111 are connected at fitting end 114.

In operation, a collector fluid is circulated, as shown by arrows F, from main unit 70 through line 108 to pass through the probe. In the probe, the collector fluid collects components of interest that permeate through membrane 109 from fluid 118 into the channels of the probe through which the collector fluid flows. The collector fluid containing components of interest then returns to main unit 70 through line 111 where the collector fluid and components therein are analyzed. The collector fluid can be circulated at pressures less than, at, or greater than the fluid pressure external to the probe, as desired.

The collector flow fluid may be selected according to the type of analytes to be monitored and may be selected to reduce their interference in the analysis/measuring process. In some embodiments, the collector fluid may be from a compressed gas system 120, including for example compressed gas cylinders or an automated compressor. In such an embodiment, compressed air, inert gas (i.e. He or Ar) or permanent gas (i.e. $N_2$) may be selected as the collector fluid and can be, for example, supplied from compressed cylinders. The collector fluid may be drawn in or accepted by the main unit and may be exhausted after it has passed through the analyzer. In another embodiment, air from the environment can be employed as the collector fluid. An example of a system employing ambient air as the collector fluid is shown and described hereinbelow in reference to FIG. 11.

The analyzer used in the process or apparatus, may be selected according to the type of analytes to be monitored and the data that is required, etc. For example, the analyzer may include any qualitative and/or quantitative form of liquid, vapor or gas sensor, detector or monitor, etc.

One particularity of using such membrane-based fluid analysis devices in monitoring liquids (and especially aqueous solutions) is that, in addition, to analytes of interest sampled by the probe, water vapor may be co-permeated. This vapor may end up condensing/freezing on the return line, or even reaching the analyzer, which might be not desired in some systems and may even damage components.

For this purpose a tubing type drying section 121 may be installed in return line 111, wherein the collector fluid may be dried by use of a tubing selected to be permeable to water vapor but impermeable to the analytes of interest being conveyed by the collector fluid. An example of such a tubing type drying section is shown in FIG. 10 and may include, for example, a semi permeable coaxial tubing as is available as Nafion™ tubing available from Perma Pure Inc., New Jersey. Section 121 includes a core tube 125 formed of a membrane permeable to water vapor but not to the component of interest and an outside jacket tube 127 that forms an annulus 129 about core tube 125. In use, the return collector fluid stream can be passed through tube 125 and annulus 129 can be swept with a drying gas flow, such as air, that collects and removes the water vapors permeated through the wall of the inner tube 125. Jacket 127 can be connected to a dessicator 131 to strip water from the drying gas flow, if desired.

In this way, the collected sample flow is dried out while transporting it, reducing or eliminating the need for a desiccant type dryer in the flow of the return line. By avoiding the need to run the return line flow itself to a dessicator, problems of attenuated or overlapped concentration peaks and lag time increases, due to the flow passing through such a dead volume, may be avoided. Moreover, the desiccant, if not regenerable on line, can be replaced without opening the main unit, or shutting off the sampling process.

In the embodiment of FIG. 10, the drying gas flow passes through a recycle circuit including a line 135 from jacket 127 to dessicator 131 and another line 137 from the dessicator back to the jacket. In this circuit, the drying gas may be flowed through section 121 and then dried before be sent back through section again. This circuit can continue with only occasional regeneration or replacement of the desiccant in dessicator 131. It is to be noted that the system can generally be operated with undried fluid for short while replacing the desiccant, without considerable adverse effects. Pumps 139 and flow regulators 140 or other means may be provided in the circuit to control flow through the section 121. A valve 142 can be provided in line 135, if desired, to permit exhaust and replacement of drying gas flow or to permit operation in an open condition.

The drying gas can be any of various gases. In one embodiment shown in FIG. 11, ambient air A can be used as both the drying gas and the collector fluid. If ambient air is used as the drying gas flow, it oftentimes requires a filtering and, especially, drying procedure before entering the main unit. As such a large volume desiccant and/or liquid drying means 150 can be installed in an air intake 152 after which a portion of the air D is flows to a line 154 to jacket 127 and a portion of the air Fa flows to a collector flow input line 108a, to act as the collector fluid. Again flow through jacket 127 can act to dry the collector fluid passing through output line 111, without adverse effects to the collector fluid lag time or concentration accuracy. Thereafter, flow from the jacket can be exhausted, for example at port 158.

Figure 11:
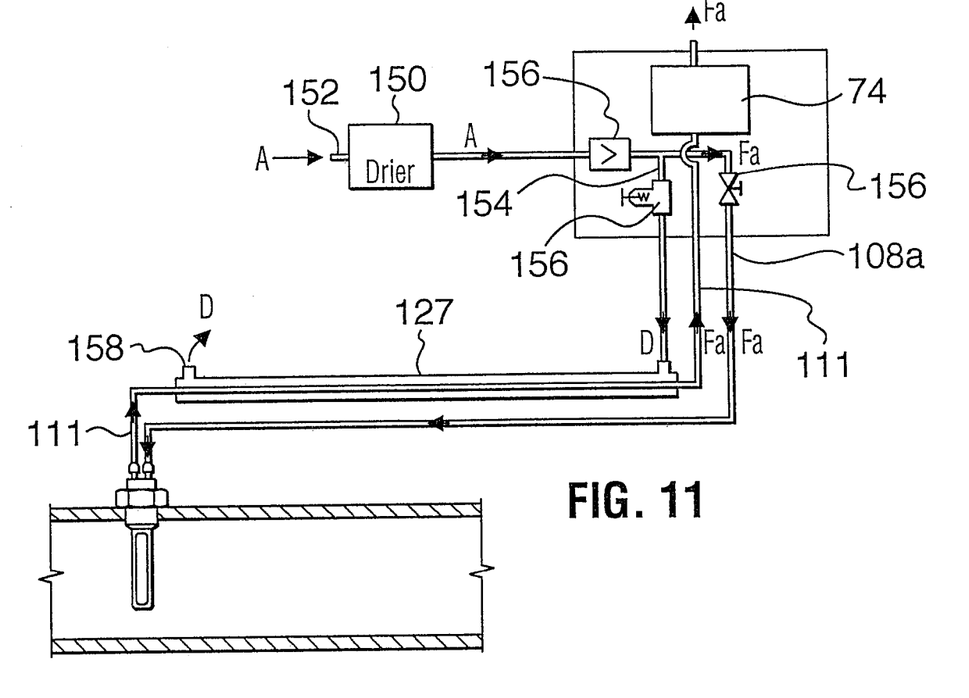
FIG. 11 is a schematic illustration of one embodiment of an apparatus according to the present invention employing a probe.

Pumps, flow regulator and valves 156 may be provided in various configurations to control flow volumes to each of these lines. For example, in one embodiment an intake pump and a relief type pressure regulator can be used in the drying fluid flow line, which would give a constant pressure for the collector fluid flow and any surplus flow could pass through the pressure relief valve regulator to the coaxial dryer section. The amount of the total intake flow in the main unit being may be set or adjusted using a fixed pneumatic valve, for example in the line prior to line 154, and the relief pressure regulator so that there is sufficient flow of drying flow through the drying section, but the desiccant can be used for a considerable period without waste, as may occur where an uncontrolled flow is permitted to pass through the jacket of the drying section.

As mentioned previously, another particularity of methods and/or apparatus using membrane sampling devices relates to the variability of the collected analytes concentration in the flow to the analyzer which may occur depending on the collector fluid flow volume used. As the collector fluid flow rate is increased through a fixed sample, the collected analyte concentration will decrease. As noted previously this is sometimes called analyte dilution or collected sample dilution. The present probe can accommodate high flow rates substantially without generation of adversely high head pressures. This makes the present method and apparatus suitable for analyte concentration control through collector flow rate control. This approach is useful, for example, when the concentration of analytes reaches undesirably high values, for which a sensor used in the analyzer is not rated or are behaving strongly nonlinear. If it is desirable to adjust the concentration of analytes at the sensor, the concentration might be diminished in a controlled way by increasing the collector flow rate by a known amount. This known change in flow rate can be applied as a correction factor to the measurements of analyte concentration taken by the analyzer, so that the final response may be independent of the flow amount value or corrected for it. In other words an analyte concentration value, corrected for flow adjustments, would be finally output no matter the flow amount, even though the analyzer may be measuring flow-dependent concentrations. In one embodiment, for example, catalytic combustible detectors may be used in an analyzer for a membrane probe and such detectors may be damaged by analyte concentrations above a particular value, for example 5% methane by volume in air. In such an embodiment, the above-noted method can be used wherein concentration is monitored and flow is increased should the analyte concentration approach 5% to ensure that the analyte concentration in the collector fluid substantially remains below 5%. However, the measured concentration may be corrected for any increase in the collector flow rate such that the finally output is representative of the actual analyte concentration in the sample fluid.

A probe, an apparatus and a method may be used to analyze various process fluids. If the process fluids are likely to cause intermittent or continuous high external pressures, such as fluids in a pressurized system, then it may be useful to employ a membrane support such as screen 52 or other means, as described in reference to FIG. 9.

In one embodiment, the process fluid may be hydrocarbon-based. In particular, probes, apparatus and methods according to the present invention have found application in the analysis of fluids from the petroleum industry including, for example, exploration, wellbore drilling, petroleum production and petroleum processing. The fluid can be, for example, drilling fluid including but not limited to water-based mud, diesel invert mud, synthetic oil-based mud, or fluids used in underbalanced drilling such as nitrogen, air, or a mixture of the above mentioned drilling fluids. In such a mudlogging application, the components of interest may be for example, hydrocarbons, vapors and/or permanent gases ($CO_2$, $N_2$).

Figure 12:
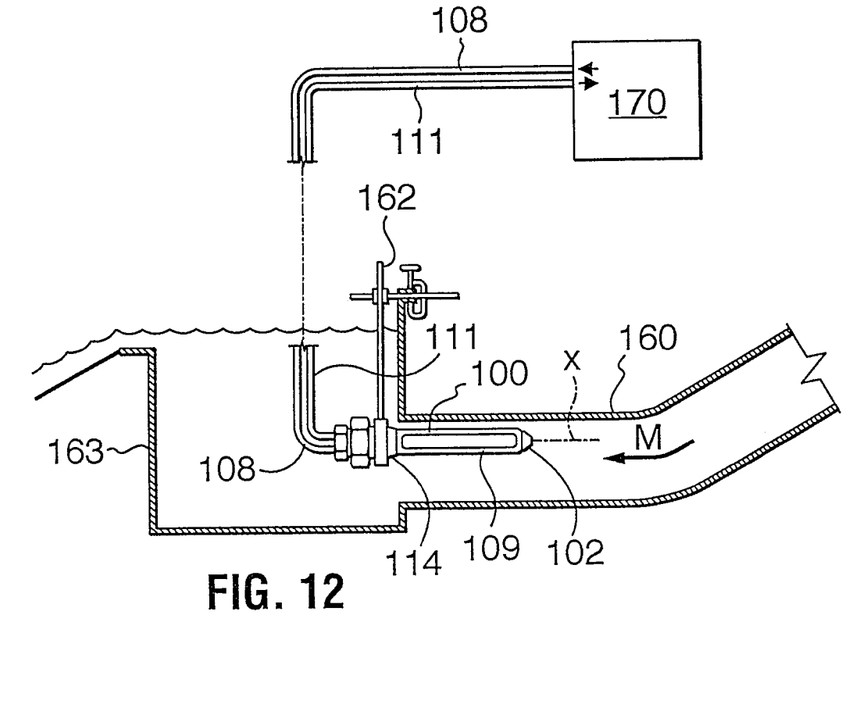
FIG. 12 is a schematic illustration of one embodiment of an apparatus according to the present invention employing a probe.

FIG. 12 shows schematically a process and apparatus for mudlogging. A membrane-based probe 100, that may, for example, be similar to one described in FIG. 1 or 9 with or without any of the various described or other options.

Probe 100 may be positioned in a mud return line 160, such as a line leading from the wellhead to a shaker pit or header box or in a blooey line, such that the mud flows therepast. In the illustrated embodiment, the probe is mounted on a bracket 162, which extends down into the shaker pit 163 to a position adjacent a outlet from the return line. When mounted on bracket 162, probe is positioned in the mud flow M passing through the return line. It will be appreciated that the form of fitting end in this embodiment may be quite different than in the apparatus of FIG. 10, since no sealing features need be included.

The probe can be positioned with its membrane stem 102 pointing into the flow such that the long axis x of the probe, from fitting end 114 to membrane stem 102, being substantially parallel to the direction of flow. As such, the plane defined by membrane 109 is parallel to flow. In this configuration, the flow of mud tends not to impinge directly on membrane 109 but flows along its length. Also, mud impingement tends to occur against the end of the probe and on fitting end 114, which parts may be selected to be formed of a durable material, such as stainless steel which can withstand impingement better than a membrane surface. Membrane 109 can be positioned with it plane in a vertical configuration such that solids tend not to settle thereon.

A collector flow input line 108 can extend from an analyzer 170 to the fitting end of sampling probe 100 and a collector fluid output line 111 can extend from fitting end 114 to the analyzer. Since the wellhead area may require higher industrial ratings, it may be desirable to position the analyzer 170 a considerable distance from the probe and increase the flow rate to reduce lag time between the probe and the analyzer.

Analyzer 170 may include detectors such as, for example, a spectrophotometer (i.e. using infrared), chromatograph, thermal conductivity or a catalytic combustible detector to monitor concentrations of analytes of interest to mudlogging some of which were noted hereinabove.

In some petroleum applications, such as in underbalanced drilling, blooey line fluids analysis, in situ production well oil or gas, pressurized tanks, etc., the fluid to be analyzed may be under pressure and therefore a membrane support may be useful. Also, the fluids to be analyzed may contain solids, such as drill cuttings or solid additives, that may impinge against the membrane during use of the probe. As such, a reinforced or supported membrane may be useful in such an application.

While the invention has been described in conjunction with the disclosed embodiments, it will be understood that the invention is not intended to be limited to these embodiments. On the contrary, the invention is intended to cover alternatives, modifications and equivalents, which may be included within the spirit and scope of the invention as defined by the appended claims.

The invention claimed is:

1. A probe for analyzing fluid concentrations in a fluid to be analyzed, the probe comprising:
   a probe body including a fitting end and a stem, the stem including an outboard end opposite the fitting end, a first side and a second side;
   a channel formed along the stem on its first side and second side, the channel extending along the first side from an inlet adjacent the fitting end toward the stem outboard end and passing to the second side to extend from the outboard end to an outlet adjacent the fitting end and the channel being formed on the stem surface at along a portion of its length; and
   a sheet-form membrane secured to the stem in a sealing configuration over the channel such that a collector fluid can pass through the channel from the inlet to the outlet, the membrane including an active surface exposed to the exterior of the probe and the collector fluid passing through the channel,
   wherein the channel includes a first open side, a second open side and a portion passing through the body to connect them and the sheet-form membrane is formed of a first membrane secured to the stem over the first open side and a second membrane secured to the stem over the second open side.

2. The probe as described in claim 1 wherein the probe body has a maximum outer dimension less than the maximum outer dimension of the fitting end.

3. The probe as described in claim 1 wherein the first membrane and the second membrane each are elongate having side edges and the first and second membranes are each clamped against the probe body by a device including a frame secured by a plurality of fasteners spaced along each of the side edges.

4. A method of analyzing a fluid for the existence therein of a component of interest, the method comprising:
   using a probe as described in claim 1;
   inserting the probe to the fluid so that at least the active area of the membrane is in contact with the fluid;
   providing a collector fluid to the probe, the collector fluid passing through and exiting the probe; and
   passing the exiting collector fluid on for analysis.

5. The method of claim 4 wherein the collector fluid is passed on to an analysis circuit.

6. The method of claim 4 wherein the collector fluid is passed on to a unit capable of determining the presence of the component of interest.

7. The method of claim 4 wherein the collector fluid is continuously or intermittently provided to the probe.

8. The method of claim 4 wherein the collector fluid is continuously or intermittently passed on for analysis.

9. The method of claim 4 wherein the exiting collector fluid is dried.

10. The method as described in claim 4 where the fluid to be analyzed is a drilling fluid including but not limited to water-based mud, diesel invert mud, synthetic oil-based mud, or fluids used in underbalanced drilling such as nitrogen, air, or a mixture of the above mentioned drilling fluids.

11. The method as described in claim 4 in an application for mudlogging and the component of interest includes one or more of hydrocarbons, vapors, permanent gases or volatiles.

12. The method as described in claim 4 wherein the collector fluid flow rate is adjusted to adjust the concentration of the component of interest in the collector fluid.

13. An apparatus for analyzing a fluid for a component of interest, the apparatus comprising:
   a probe as described in claim 1;
   a mounting configuration to install the probe in the process fluid to be analyzed;
   a main unit including any of an analyzer, a flow conditioning/measuring device for a collector fluid, or a power supply; and
   connections between the main unit and the probe including an incoming flow line from the main unit to the probe and an outcoming flow line from the probe to the main unit.

14. The apparatus as described in claim 13 where the collector fluid is air.

15. The apparatus as in claim 13 further comprising a membrane coaxial tubing in the outcoming flow line such that the outcoming flow from the probe to the main unit is dried during transport therethrough.

16. The apparatus as in claim 15 wherein the coaxial tubing accommodates the collector flow in its inner core and a flow of drying gas through an outer annulus.

17. The apparatus as in claim 13 further comprising flow control means and wherein a sample concentration range brought to the main unit by the collector fluid is switched using selected flow values for the collector fluid.

18. The apparatus as in claim 13 wherein the analyzer includes a catalytic combustible detector, a spectrophotometer, a chromatograph or a thermal conductive detector.

19. A method of analyzing a sample fluid for the existence of a component of interest, the method comprising:
   providing a probe as described in claim 1 wherein the membrane is permeable to the component of interest;
   providing an analyzer, the analyzer being effective at a selected concentration range for the component of interest;
   inserting the probe to the sample fluid so that at least the active area of the membrane is in contact with the sample fluid;
   providing a collector fluid to the probe, the collector fluid passing through and exiting the probe;
   passing the exiting collector fluid to the analyzer for analysis for determination of the measured concentration of the component of interest; and
   adjusting the collector fluid flow rate to bring the measured concentration into the selected concentration range in which the analyzer is effective.

20. The method of claim 19 wherein the analyzer includes a catalytic combustible detector and the flow rate is adjusted to maintain the measured concentration below an upper limit of the selected concentration range in which the detector is effective.

21. The method of claim 19 wherein the exiting collector fluid is dried by passing through a membrane coaxial tubing.

* * * * *